United States Patent [19]

Kaschig

[11] Patent Number: 4,477,673
[45] Date of Patent: Oct. 16, 1984

[54] PROCESS FOR THE PREPARATION OF SUBSTITUTED DIVINYLPYRIDINES AND NOVEL SUBSTITUTED DIVINYLPYRIDINES

[75] Inventor: Jürgen Kaschig, Ardsley, N.Y.

[73] Assignee: Ciba-Geigy Corporation, Ardsley, N.Y.

[21] Appl. No.: 458,232

[22] Filed: Jan. 17, 1983

[30] Foreign Application Priority Data

Jan. 27, 1982 [CH] Switzerland ............................ 501/82

[51] Int. Cl.³ .................. C07D 213/30; C07D 213/16; C07D 213/26; C07D 213/57
[52] U.S. Cl. .................................... 546/344; 546/350; 546/22; 546/250; 546/253; 546/346; 546/352
[58] Field of Search ................. 546/22, 250, 253, 350, 546/352, 344, 346

[56] References Cited

U.S. PATENT DOCUMENTS 3,467,663  9/1969  Ineno et al. .......................... 546/344
4,266,061  5/1981  Bonnemann et al. ............... 546/253

FOREIGN PATENT DOCUMENTS 42-8620  4/1967  Japan .................................... 546/344

OTHER PUBLICATIONS

Chemical Abstracts vol. 55, col. 18721i, (1961) Abstracting Bodalski et al. "Bull. Acad. Polon. Sci., Ser. Sci. Chim." vol. 8, pp. 217-218 (1960).

Primary Examiner—Robert T. Bond
Attorney, Agent, or Firm—Michael W. Glynn

[57] ABSTRACT

The invention relates to compounds of the formula I

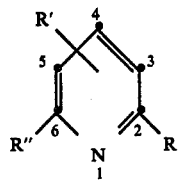

(I)

wherein R' is bound in the 4- or 5-position, R and R' are $-CH_2OH$, $-CH_2CH_2OH$, $-CH_2CH_2OCH_2C_6H_5$, $-CH_2-X$, $-CH_2P^{\oplus}(Y)_3X^{\ominus}$, $-CH_2P(O)(C_{1-3}alkoxy)_2$ or $-CH=CH_2$, R" is $C_{1-10}$alkyl, X is a halogen atom, $X^{\ominus}$ is the anion corresponding to X and Y is phenyl or phenyl which is substituted by a $C_1-C_5$alkyl group. These compounds can be obtained by a novel simple process in good to very good yield by co-cyclotrimerizing nitriles R"—CN with alkynes $HC\equiv C-Z$ (Z is $-CH_2OH$, $-CH_2CH_2OH$ or $-CH_2CH_2OCH_2C_6H_5$), in the presence of a cobalt(I) catalyst, dehydrating the resultant pyridines either to compounds of the formula I, in which R and R" are $-CH=CH_2$, or converting them into the corresponding bishalomethylpyridines, reacting these latter with triphenylphosphines or trialkylphosphites and subjecting the pyridinephosphonium salts or pyridinephosphonic acid tetraalkyl esters so obtained to a Wittig or Wittig-Horner reaction. Compounds of the formula (I), in which R and R" are $-CH=CH_2$, can also be obtained by direct reaction of nitriles R"—CN with vinyl acetylene in the presence of cobalt(I) catalysts, and are used e.g. as crosslinking agents or for the production of polymers.

20 Claims, No Drawings

PROCESS FOR THE PREPARATION OF SUBSTITUTED DIVINYLPYRIDINES AND NOVEL SUBSTITUTED DIVINYLPYRIDINES

The present invention relates to a novel process for the preparation of 6-substituted divinylpyridines and to the novel divinylpyridines and intermediates obtainable thereby. Unsubstituted divinylpyridines or divinylpyridines which are substituted in the 4- or 6-position by a methyl group can be obtained, e.g. by heating dimethylpyridines or trimethylpyridines with formaldehyde to give the corresponding bis-β-hydroxyethylpyridines and then dehydrating these reaction products. Methylvinyl- or methylethylpyridines can be reacted in corresponding manner to give divinylpyridines, except that the vinylethylpyridine obtained from starting methylethylpyridines after dehydration must additionally be catalytically hydrogenated. Aside from unsubstituted divinylpyridines, 2,6-divinyl-4-methylpyridine and 2,4-divinyl-6-methylpyridine have also been prepared in this manner. Reference is made in this connection e.g. to the following publications: Bull. Acad.Polon.Sci., Sér.Sci.chim., 8, 217 (1960); Roczniki chem. 29, 141(1955), 38, 1337(1964) and 40, 1505(1966); Zhur.-Prikl.Khimii, 45(4), 872(1972), U.S. Pat. No. 2,739,948, Russian Pat. No. 234 407, French Pat. No. 1 525 475 and GDR patent 54 361. Unsubstituted divinylpyridines can also be obtained in the temperature range from about 450° to 800° C. by catalytic dehydrogenation of diethyl pyridines or ethylvinyl pyridines [U.S. Pat. Nos. 2,728,770 and 2,611,769, and German Offenlegungsschrift No. 2 061 241]. Finally, 2,5-divinylpyridine can also be prepared by Mannich reaction from 2-methyl-5-vinylpyridine [Khim. Geterotsikl. Soedin., 4, 667 (1967)]. In these known prior art processes, some of the starting materials are difficult to obtain and, in particular, the divinylpyridines are obtained in unsatisfactory yield (usually less than 10%, based on the starting pyridine).

A novel process has now been found by means of which it is possible to prepare 6-substituted divinylpyridines and precursors thereof, under relatively mild reaction conditions and using readily accessible and cheap starting materials, in good to very good yield.

Accordingly, the present invention provides a process for the preparation of compounds of the formula I

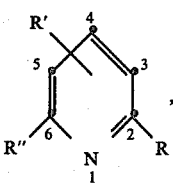

(I)

wherein
R' is bound in the 4- or 5-position,
R and R' are —CH$_2$OH, —CH$_2$CH$_2$OH, —CH$_2$CH$_2$OCH$_2$C$_6$H$_5$, —CH$_2$—X, —CH$_2$P$^\oplus$(Y)$_3$X$^\ominus$, —CH$_2$P(O)(C$_{1-3}$alkoxy)$_2$ or —CH=CH$_2$,
R" is C$_{1-10}$alkyl,
X is a halogen atom such as a chlorine, bromine or iodine atom, preferably a chlorine atom and, most preferably, a bromine atom,
X$^\ominus$ is the anion corresponding to X and
Y is phenyl which may be substituted by a C$_1$-C$_5$alkyl group, which process comprises reacting a compound of the formula II

(II)

with a compound of the formula III

(III)

in the temperature range from 40° to 180° C. and in the presence of a cobalt(I) catalyst, to give a compound of the formula IV

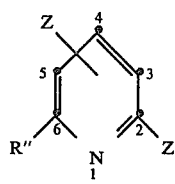

(IV)

wherein R" is a defined for formula I and Z is —CH$_2$OH, —CH$_2$CH$_2$OH or —CH$_2$CH$_2$OCH$_2$C$_6$H$_5$, and dehydrating a compound of the formula IV, wherein Z is —CH$_2$CH$_2$OH or —CH$_2$CH$_2$OCH$_2$C$_6$H$_5$, if desired after previously hydrogenating —CH$_2$CH$_2$OCH$_2$C$_6$H$_5$ groups to —CH$_2$CH$_2$OH groups, to give compounds of the formula I, wherein R and R' are —CH=CH$_2$, and reacting a compound of the formula IV, in which Z is —CH$_2$OH, by treatment with a halogenating agent to give a compound of the formula V

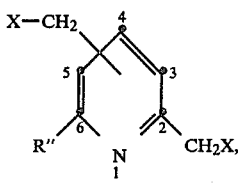

(V)

reacting the compound of the formula V with a compound of the formula VIa and VIb

         (VIa)

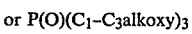         (VIb)

to give a compound of the formula VIIa and VIIb

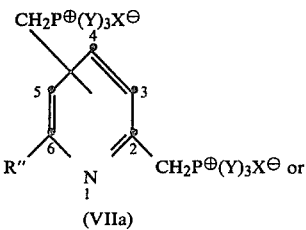

(VIIa)

-continued

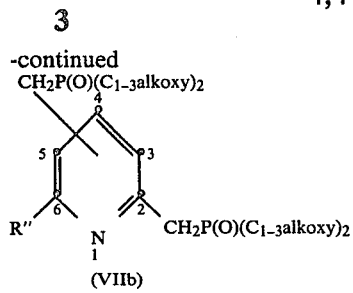
(VIIb)

and reacting the compound of the formula VIIa and VIIb with formaldehyde, in the presence of a base, to give a compound of the formula I, in which R and R' are —CH=CH$_2$ (Wittig or Wittig-Horner reaction). In the formulae above, R", Y, X and X$^\ominus$ are as defined for formula I and the second group Z, —CH$_2$-halogen, —CH$_2$P$^\oplus$(Y)$_3$X$^\ominus$ or —CH$_2$P(O)(C$_1$-C$_3$alkoxy)$_2$ are linked to the pyridine ring in the 4- or 5-position.

It is surprising that nitriles of the formula II can be cyclotrimerised in the presence of cobalt(I) catalysts, i.e. strong Lewis acids, with alkynes of the formula III containing OH groups to give pyridine derivatives of the formula IV. It is known that the reaction of nitriles with alcohols, e.g. propargyl alcohol, in the presence of acid or basic catalysts such as HCl, HBr, sodium methoxide or sodium ethoxide, results in the formation of iminoethers. These iminoethers can be converted in the presence of salts of metals of Groups IB, IIb and VIIIb, e.g. AG(I) salts and Hg(I) salts, into oxazole derivatives by intramolecular cyclisation [see, e.g., Chem. Review 61, 179 (1961); J. Org. Chem. 26, 412 (1961); and German Offenlegungsschrift No. 21 52 367]. Nitriles such as benzonitrile and acetonitrile can also be reacted direct, in the presence of specific strong acids such as sulfuric acid, phosphoric acid and polyphosphoric acid, with α-acetylene alcohols to give oxazole derivatives (Japanese published patent specification No. 29849/64).

Compounds of the formula I, wherein R and R' are —CH=CH$_2$ and R" has the given meaning, can also be prepared by a modified process by reacting a compound of the formula II with vinyl acetylene in the temperature range from 30° to 170° C., preferably from 100° to 160° C., and in the presence of a cobalt(I) catalyst.

The reaction is preferably carried out continuously. Surprisingly, the divinylpyridines are obtained in this modified process as main products, although the reaction of conjugated acetylenes, such as vinyl acetylene, methyl propiolate and phenyl acetylene, with nitriles in the presence of cobalt catalysts according to U.S. Pat. No. 3,829,429 yields principally oligomerisation products of the conjugated acetylenes. This U.S. patent does not specifically describe the preparation of 6-substituted divinylpyridines.

Mixtures of isomers obtained in the process of this invention may be separated, if desired, by conventional methods, e.g. by crystallisation. Alkyl groups R", alkoxy moieties of radicals R and R' and alkyl substituents at phenyl groups Y may be straight chain or branched. Typical examples of alkyl groups R" are: methyl, ethyl, n-propyl, isopropyl, n-butyl, sec-butyl, n-pentyl, pent-2-yl, n-hexyl, 2-ethyl-hexyl, n-heptyl, n-octyl, n-nonyl and n-dodecyl. R" is preferably straight chain or branched C$_1$–C$_4$alkyl, most preferably methyl.

Examples of alkoxy moieties of radicals R and R' are methoxy, ethoxy, n-propoxy and isopropoxy. Preferred alkoxy groups are ethoxy and isopropoxy.

If phenyl groups Y are substituted by C$_1$-C$_5$alkyl, examples of such alkyl substituents are methyl, ethyl, n-propyl, isopropyl, n-butyl and n-pentyl groups, with methyl or ethyl groups being preferred. Most preferably, however, Y is unsubstituted phenyl.

X is preferably chlorine and most preferably bromine. Z is preferably —CH$_2$CH$_2$OH and most preferably —CH$_2$OH. The compounds of the formula IV and their derivatives of the formula V, VIIa and VIIb, are usually obtained as mixtures of isomers. Mixtures of isomers of compounds of the formula IV, in which Z is —CH$_2$OH, and the derivatives obtainable therefrom, can be separated into the individual isomers in particularly simple manner, e.g., by crystallisation in suitable solvents or solvent mixtures, such as acetone/diethyl ether or N,N-dimethylformamide.

The cobalt(I) catalysts employed for the co-cyclotrimerisation of the nitriles of formula II with the alkynes or formula III, as well as in the modified process for the direct preparation of divinylpyridines of the formula I, may be the known compounds described e.g. in Synthesis Communications, 575 (1964) and 26 (1976), and also in U.S. Pat. No. 4,006,149 and German Offenlegungsschrift No. 27 42 541.

Examples of suitable catalysts are biscyclopentadienylcobalt (cobaltocene) which may also be substituted at one cyclopentadienyl group e.g. by —CH$_2$CN, —CH(CN)—CH$_3$, —C(CN)=CH$_2$ or —CH(CN)CH$_2$OCH$_3$, biscyclopentadienyltetraphenylcobalt, cyclopentadienyl-cobalt-cyclooctadiene, $\eta^3$-cyclooctadienyl-cobalt-cyloocatadiene, methylheptadienyl-cobalt-butadiene. The cobalt catalysts may be used as such or prepared in situ by reduction of divalent or trivalent cobalt salts of inorganic or organic acids. Examples of suitable cobalt salts are cobalt(II) chloride, cobalt(II) fluoride, cobalt(II) carbonate, cobalt(II) hydroxide carbonate, cobalt(II) sulfate, cobalt(II) nitrate, cobalt(II) formate, cobalt(II) acetate, cobalt(II) acetylacetonate, cobalt(II) ethylate, cobalt(II) n-butylate, cobalt(II) oxalate, cobalt(II) phenolate and cobalt(II) naphthenate as well as cobalt(III) acetylacetonate. Suitable reducing agents are metals of groups I to III of the Periodic Table and, in particular, hydrides thereof, such as lithium, sodium, magnesium, calcium, LiH, LiAlH$_4$ and NaBH$_4$. The preferred reducing agent is NaBH$_4$. In the process of this invention the most preferred catalyst is cyclopentadienyl-cobalt-cyclooctadiene.

The catalyst is conveniently employed in an amount of 0.1 to 3 mole%, preferably of 0.1 to 1 mole%, based on the alkyne of the formula III.

The reaction temperature for the co-cyclotrimerisation is preferably in the range from 80° to 160° C., most preferably from 140° to 150° C. The process is optionally carried out under pressure.

The reaction may be conducted in the presence of an inert organic solvent, e.g. an aliphatic or aromatic hydrocarbon such as benzene, toluene, xylenes, n-pentane, n-hexane of n-heptane; or an aliphatic or cyclic ether such as diethyl ether, diisopropyl ether, methyl ethyl ether, tetrahydropyran, tetrahydrofuran or dioxan.

The nitrile of the formula II is conveniently employed in excess of the stoichiometric amount required, preferably in 5- to 20-fold excess, in which cases the excess of nitrile also acts as solvent.

The hydrogenation of compounds of the formula IV, wherein Z is —CH$_2$CH$_2$OCH$_2$C$_6$H$_5$, to give compounds of the formula IV, wherein Z is —CH$_2$CH$_2$OH, is preferably carried out in the presence of an inert organic solvent. Examples of suitable solvents are ethanol, methanol, or dioxan, and especially acid media such as ethanol/hydrogen chloride mixtures, acetic acid or trifluoroacetic acid. Trifluoroacetic acid or a mixture thereof with acetic acid is preferred. It is advantageous to carry out the hydrogenation catalytically. Examples of suitable catalysts are copper chromium oxide and nickel catalysts such as Raney nickel, and especially noble metal catalysts such as platinum and palladium catalysts, most particularly palladium on carbon catalysts. The dehydration of compounds of the formula IV, in which Z is —$CH_2CH_2OH$, can be carried out in a manner known per se, preferably in the presence of NaOH or KOH. It is preferably carried out without a solvent in the temperature range from 130° to 200° C. and conveniently using a polymerisation inhibitor, e.g. a dinitrochloroaniline, a phenothiazine derivative, a diarylamine, sulfur, picric acid, α-nitroso-β-naphthol, hydroquinone, or a phenol such as 2,6-di-tert-butyl-p-cresol.

Halogenating agents which may be used in the reaction with compounds of the formula IV, wherein Z is —$CH_2OH$, are e.g. hydrochloric acid, hydrobromic acid or hydriodic acid, phosphoroxy chloride, thionyl chloride or thionyl bromide. It is preferred to use concentrated aqueous hydrochloric acid and, in particular, concentrated aqueous hydrobromic acid. The reaction is ordinarily carried out at reflux temperature.

The further reaction with the phosphines of the formula VIa or the phosphorous acid esters of the formula VIb is conveniently carried out in the presence of an inert organic solvent such as toluene, tetrahydrofuran or N,N-dimethylformamide, and in the temperature range from 50° to 150° C.

The reaction of the compounds of the formulae VIIa and VIIb with formaldehyde is carried out in the presence of a base and optionally of a solvent, a phase transfer catalyst and/or of a polymerisation inhibitor. Examples of suitable bases are sodium hydride, n-butyl lithium, alcoholates, hydroxides and carbonates of alkali metals and alkaline earth metals, as well as trialkylamines containing 2 to 4 carbon atoms in each of the alkyl moieties. It is preferred to use an inert solvent in the reaction, e.g. benzene, chlorobenzene, toluene, tetrahydrofuran, dioxan, N,N-dimethylformamide, dichloromethane, methanol, ethanol or water. Preferred solvents are water and, in particular, two-phase systems of water and a water-insoluble organic solvent such as dichloromethane. Preferred bases are alkali metal hydroxides or carbonates. Suitable phase transfer catalysts are e.g. crown ethers, cryptants, tetraalkylammonium salts, tetraalkylaminium salts or tetraalkylphosphonium salts as tetra-n-butylammonium hydrogen sulfate and tetra-n-butylammonium hydrogen cyanide, and tetra-n-butylaminium iodide. Suitable polymerisation inhibitors are those previously referred to above.

With the exception of 2,4-bis-(β-hydroxyethyl)-6-methylpyridine and 2,4-divinyl-6-methylpyridine, the compounds of formula I are novel and also constitute an object of the present invention. In this connection, the preferred meanings of R, R', R", X and Y are the same as those previously indicated above.

The process of this invention makes it possible for the first time to prepare 6-substituted divinylpyridines and the intermediates of the formulae IV, V, VIIa and VIIb in economic yield, and also to obtain some of these compounds in particularly simple manner in non-isomeric form, which can be advantageous when they are further used in certain cases. Divinylpyridines of the formula I can be used e.g. for obtaining polymers (ion exchange resins; see e.g. U.S. Pat. Nos. 2,739,948 and 2,824,844) or as crosslinking agents. A particularly preferred product is 2,5-divinyl-6-methylpyridine which, in contradistinction to the prior art isomer, can also be used for the production of valuable fluorescent whitening agents of the stilbene type, e.g. by reacting it with bromobenzonitriles as described in the Examples.

EXAMPLE 1

2,4-Bis(hydroxymethyl)-6-methylpyridine and 2,5-bis(hydroxymethyl)-6-methylpyridine (a) Preparation using a pressure reactor A solution of 492 g (12 moles) of acetonitrile, 168 g (3 moles) of propargyl alcohol and 4.5 g (0.0195 mole) of cyclopentadienyl-cobalt-cycloocta-(1,5)-diene is heated in a 1 liter steel autoclave under nitrogen for 3 hours to 145° C., whereupon the pressure rises to $8 \times 10^5$ Pa. After 7 hours the contents of the reactor are cooled to room temperature. After distilling off excess acetonitrile at about $1.5 \times 10^3$ Pa, a sample of the residual oil is dissolved in benzyl alcohol and titrated with anhydrous perchloric acid. A 78% reaction to substituted pyridines is found.

The crude product is dissolved in semiconcentrated hydrochloric acid (pH 1), then about the same volume of chloroform is added and the batch is heated to the boil for 3 hours with the addition of activated carbon. After cooling and filtration, the chloroform phase is separated and the aqueous phase is made alkaline with potassium carbonate and concentrated at about $1.5 \times 10^3$ Pa. Toluene is added and residual water is then removed as an azeotrope by distillation at about $2 \times 10^3$ Pa. The residue is extracted with three 250 ml portions of ethanol at 60°–70° C. The residual salts are removed by filtration and the combined filtrates are concentrated at $1.5 \times 10^3$ Pa. The residue is distilled in a high vacuum. Boiling point: 168°–180° C./$1.33 \times 10^{-3}$ Pa. Yield: 165 g (71.8% of theory) of a mixture of isomers consisting of 2,4- and 2,5-bis(hydroxymethyl)-6-methylpyridine.

The highly viscous residue (40 g) is a mixture of about 30% of product (titrated) and trishydroxymethylbenzenes. The distillate congeals on standing to a compact crystalline solid. Melting point: 70°–100° C. (picrate: m.p. 98°–110° C.; picrolonate: m.p. 169°–172° C.).

The ratio of the isomers is determined by gas chromatography (capillary column: K20M; 35.4 m): 57% of the 2,4,6-isomer and 43% of the 2,5,6-isomer.

(b) Preparation under reflux conditions

A solution of 16.4 g (0.4 mole) of acetonitrile, 11.2 g (0.2 mole) of propargyl alcohol and 1.4 g (6.03 mmoles) of cyclopentadienyl-cobalt-cycloocta-(1,5)-diene is heated in an argon atmosphere for 40 hours to 85° C. Working up is as described in Example 1a, affording 11.2 g of a crude product (undistilled) consisting of 53% of 2,4-bishydroxymethyl-6-methylpyridine, 38% of 2,5-bishydroxymethyl-6-methylpyridine and 8% of trishydroxymethylbenzenes (gas chromatographic analysis as in Example 1a). Yield of substituted pyridines: 59% of theory.

(c) Separation of isomers 535 g of the (undistilled) crude product obtained in (a) are crystallised by cooling to 4° C. The partially crystalline mixture is treated at low temperature with a mixture of 500 ml of acetone and 100 ml of diethyl ether and filtered. The filter residue is washed with acetone/diethyl ether (5:1) and recrystallised from acetone, yielding 54 g of white crystals of 2,4-bis(hydroxymethyl)-6-methylpyridine with a melting point of 106°–109° C. (picrate: m.p. 125°–128° C.).

$^1$H-NMR (CDCl$_3$+DMSO-d$_6$): δ=2.38 (s; 3H), 4.47 (s; 2H), 4.53 (s; 2H), 5.23 (s, broad; 2H), 6.90 (s; 1H) and 7.12 ppm (s; 1H).

10 g of the purified and completely crystallised mixture of isomers (obtained in Example 1a) are recrystallised from 600 ml of xylene, affording 0.5 g of 2,5-bis(hydroxymethyl)-6-methylpyridine in the form of white crystal needles with a melting point of 94°–96° C.

$^1$H-NMR (CDCl$_3$+DMSO-d$_6$): δ=2.37 (s; 3H), 4.46 (s; 2H), 4.51 (s; 2H), 4.88 (s, broad; 2H), 7.12 (d, J=8 Hz; 1H) and 7.59 ppm (d, J=8 Hz; 1H).

(d) Hydrochloride 150 ml of a solution of HCl in ethanol are added at 20° C. to 11 g of a mixture of isomers (undistilled crude product) prepared according to either Example 1a and 1b. The product is crystallised at low temperature by concentrating the solution in vacuo and adding acetone to the residue. The product is filtered with suction, washed with acetone and dried over phosphorus pentoxide, affording 7.4 g of hygroscopic crystals. Analysis for C$_8$H$_{12}$ClNO$_2$ (0.07 H$_2$O): calculated: C 50.67% H 6.38% N 7.39% Cl 18.69%; found: C 50.40% H 6.38% N 7.37% Cl 18.56%.

EXAMPLE 2

2,4-Bis(2-hydroxymethyl)-6-methylpyridine and 2,5-bis(2-hydroxyethyl)-6-methylpyridine Method A Following the procedure of Example 1b, 21.03 g (0.3 mole) of 3-butyn-1-ol, 24.6 g (0.6 mole) of acetonitrile and 1.5 g (6.46 mmoles) of cyclopentadienyl-cobalt-cycloocta-(1,5)-diene are reacted. Working up is as described in Example 1a, affording 10.2 g of an oily crude product consisting of 45% of 2,4-bis(2-hydroxyethyl)-6-methylpyridine, 35% of 2,5-bis-(2-hydroxyethyl)-6-methylpyridine and 9% of tris(2-hydroxyethyl)-benzenes (analysis by gas chromatography as in Example 1a). Yield of substituted pyridines: 30% of theory.

Method B 1.95 g (5.4 mmoles) of a mixture of isomers consisting of 2,4- and 2,5-bis(2-benzyloxyethyl)-6-methylpyridine prepared according to Example 3 are dissolved in 10 ml of trifluoroacetic acid. After addition of 0.2 g of palladium on carbon (5% by weight of Pd), hydrogenation is carried out at 20°–25° C. The uptake of hydrogen ceases after about 3 hours (233 ml=104% of theory). The catalyst is removed by filtration and then the solvent is stripped off in vacuo and the oily residue is dissolved in 2N hydrochloric acid. The solution is washed with ethyl acetate and then made alkaline (pH 9) with potassium carbonate. The product is extracted with ethyl acetate. The extract is washed with a saturated solution of sodium chloride, dried over sodium sulfate, and the solvent is then distilled off in vacuo. Yield: 9 g of an oily product.

$^1$H-NMR (CDCl$_3$): δ=2.43 and 2.47 (s; 3H), 2.68 to 2.95 (m; 4H), 3.70 to 3.95 (m; 4H), 4.08 (s; 2H) and 6.83 to 7.42 ppm (m; 2H).

(b) 2,5-Bis(2-hydroxyethyl)-6-methylpyridine 9.4 g of the product obtained by Method A are chromatographed through a 1 meter silica gel column of 6 cm diameter with a 1:5 mixture of toluene/acetone as eluant. The first fraction (1050 ml) is a solution which is concentrated to give 0.53 g of an oil which, on standing, congeals to crystals. The crystals are washed with a small amount of acetone and dried. Melting point: 82°–84° C.

$^1$H-NMR (CDCl$_3$): δ=2.48 (s; 3H); 2.73 to 2.95 (m; 4H), 3.71 to 3.97 (m; 6H), 6.90 (d, J=8 Hz, 1H) and 7.38 ppm (d, J=8 Hz; 1H).

EXAMPLE 3

2,4-Bis(2-benzyloxyethyl)-6-methylpyridine and 2,5-bis(2-benzyloxyethyl)-6-methylpyridine Following the procedure of Example 1b, 18.4 g (0.115 mole) of 4-benzyloxy-1-butyne, 24.6 g (0.6 mole) of acetonitrile and 1.5 g (6.46 mmoles) of cyclopentadienyl-cobalt-cycloocta-(1,5)-diene are reacted. The reaction mixture is acidified with 200 ml of semiconcentrated hydrochloric acid and the mixture is extracted with two 150 ml portions of ethyl acetate. To the aqueous solution is added a solution of 4 g of 1-nitroso-2-naphthol in 200 ml of semiconcentrated acetic acid. The precipitated cobalt complex is filtered with suction. The filtrate is washed with diethyl ether and then made alkaline with potassium carbonate. The product is extracted with ethyl acetate. The extract is dried over sodium sulfate and the solvent is stripped off in vacuo, affording 2.9 g of a crude product which is distilled in a bulb tube. Yield: 2.3 g (6%) of an oil with a boiling point of about 190°–220° C./0.13 Pa; n$_D^{20}$=1.5652.

Analysis for C$_{24}$N$_{27}$NO$_2$: calculated: C 79.74% H 7.53% N 3.87% O 8.85%; found: C 79.68% H 7.62% N 3.94% O 9.09%.

EXAMPLE 4

2,4-Bis(bromomethyl)-6-methylpyridine

A solution of 45 g (0.294 mole) of 2,4-bis(hydroxymethyl)-6-methylpyridine and 160 ml of 62% hydrobromic acid is heated for 20 hours to the boil. The reaction mixture is then diluted with 250 ml of water and concentrated at 1.5×10$^3$ Pa. The residue is dissolved in 150 ml of water and a layer of 250 ml of diethyl ether is added to the solution. With vigorous stirring, the aqueous phase is made alkaline (pH 8) by addition of solid potassium carbonate. The ether phase is then separated and the aqueous phase is washed with diethyl ether. The combined ether phases are dried over sodium sulfate and concentrated at 1.5×10$^3$ Pa, leaving as residue a red viscous oil. Yield: 76 g (93% of theory). The product is unstable at room temperature and is further used immediately.

(b) 2,4-Bis(bromomethyl)-6-methylpyridine and 2,5-bis(bromomethyl)-6-methylpyridine Method A Following the procedure of Example 4a, 77.4 g (0.5 mole) of the mixture of isomers obtained in Example 1a are reacted with 270 ml of hydrobromic acid. Yield: 124 g (89% of theory) of an oily product which congeals at 4° C. to a semicrystalline solid. The picrolonate has a melting point of 143°–144° C.

¹H-NMR (CDCl₃): δ=2.50 and 2.57 (s; 3H), 4.28, 4.39 and 4.43 (s; 4H), 7.02 (s), 7.20 (s), 7.20 (d, J=8 Hz) and 7.54 ppm (d, J=8 Hz; together 2H).

Method B

Following the procedure of Example 4a, 9 g (47 mmoles) of the hydrochloride of the mixture of isomers obtained in Example 1d are reacted with 40 ml of hydrobromic acid. Yield: 9.35 g (71% of theory) of a product which is identical to the product obtained by Method A.

EXAMPLE 5

[6-Methylpyridine-2,5-diyl-bis(methylene)]bis-triphenylphosphonium dibromide

A solution of 630 g (2.4 moles) of triphenylphosphine and 1.5 liters of N,N-dimethylformamide is heated to 80° C. A solution of 279 g of the mixture of isomers obtained in Example 4b and 500 ml of N,N-dimethylformamide is added dropwise. The batch is stirred for 3 hours at 80° C. and then cooled to room temperature. Fine crystals precipitate over the course of several hours. These crystals are filtered with suction, washed with 200 ml of cold N,N-dimethylformamide and 2 liters of diethyl ether and recrystallised from water. Yield: 215 g.

Analysis for $C_{44}H_{39}NBr_2P_2$: calculated: C 65.77% H 4.89% N 1.74% Br 19.89%; found: C 65.95% H 4.90% N 1.76% Br 19.85%.

The bulk of the solvent is stripped off from the mother liquor at $1.5 \times 10^3$ Pa and the residue is dissolved in dichloromethane. The solution is stirred into diethyl ether and a finely powdered precipitate is obtained as further product. Yield: 479 g of a mixture of isomers consisting of [6-methylpyridine-2,5-diyl-bis(methylene)]bistriphenylphosphonium dibromide and [6-methylpyridine-2,4-diyl-bis-(methylene)]bistriphenylphosphonium dibromide.

¹H-NMR (CDCl₃): δ=1.61 and 1.97 (s; 3H), 5.33 and 5.61 (d, J=15 Hz; 4H) and 7.32 to 8.00 ppm (m, 32 arom. H).

Total yield of triphenylphosphonium bromides: 86.4% of theory.

EXAMPLE 6

[6-Methylpyridine-2,4-diyl-bis(methylene)]bis-triphenylphosphonium dibromide

Following the procedure of Example 5, 169 g (0.645 mole) of trisphenylphosphine are reacted with 75 g (0.269 mole) of 2,4-bis(bromomethyl)-6-methylpyridine obtained in Example 4a. The product is isolated in the form of a finely powdered precipitate by stirring the dichloromethane solution into ethyl acetate. Yield: 198.3 g (92% of theory); m.p. 220°–225° C.

EXAMPLE 7

Tetraethyl [6-methylpyridine-2,4-diyl-bis(methylene)]bisphosphonate and tetraethyl [6-methylpyridine-2,5-diyl-bis(methylene)]bisphosphonate A mixture of 36.6 g (0.131 mole) of the bis-bromomethyl picoline of Example 4b, 47.9 g (0.288 mole) of triethylphosphite and 140 ml of xylene is heated to the boil. The boiling constituents are distilled off by gradually raising the bath temperature to 200° C. The residual viscous oil is dried at 50° C./0.13 Pa. Yield: 47 g (91% of theory). Boiling point: about 230° C./0.13 Pa (bulb tube distillation).

Analysis for $C_{16}N_{29}NO_6P_2$: calculated: C 48.85% H 7.43% N 3.56% P 15.75%; found: C 48.67% H 7.90% N 3.89% P 15.54%.

EXAMPLE 8

2,5-Divinyl-6-methylpyridine

With rapid stirring, a solution of 120 g (3 moles) of sodium hydroxide and 240 ml of water is added dropwise over 1½ hours to a mixture of 165 g (0.205 mole) of [6-methylpyridine-2,5-diyl-bis(methylene)]bistriphenylphosphonium dibromide (Example 5), 1.2 liters of 38% aqueous formaldehyde solution, 1 liter of dichloromethane and 1.07 g (4 mmoles) of tetrabutylammonium cyanide. During the addition the temperature is kept at 15° C. After stirring for 16 hours at room temperature, the organic phase is separated and the aqueous phase is washed with 200 ml of dichloromethane. The combined organic phases are washed with 1½ liters of water and, after addition of 100 mg of 2,6-di-tert-butyl-p-cresol, concentrated at $1.5 \times 10^3$ Pa. The semi-solid residue is stirred in 1.4 liters of hydrochloric acid (concentration: about 10%). The batch is extracted with two 600 ml portions of ethyl acetate and then 100 mg of 2,6-di-tert-butyl-p-cresol and 700 ml of ethyl acetate are added to the aqueous phase. The mixture is made alkaline with solid potassium carbonate and the organic phase is separated, dried over sodium sulfate and concentrated at $1.5 \times 10^3$ Pa. The liquid crude product is then distilled; b.p. 38°–40° C./6.7 Pa; yield 26.5 g (89% of theory); $n_D^{20}$=1.5819.

¹H-NMR (CDCl₃): δ=2.59 (s; 3H), 5.33 (m, J=1.5 Hz and 10 Hz; 1H), 5.43 (m, J=1.5 Hz and 10 Hz; 1H), 5.63 (m, J=1.5 Hz and 18 Hz; 1H), 6.15 (m; J=2.0 Hz and 18 Hz; 1H), 6.80 (m; J=10 Hz and 18 Hz; 1H), 6.89 (m; J=10 Hz and 18 Hz; 1H), 7.18 (d, J=8 Hz; 1H) and 7.68 ppm (d, J=8 Hz; 1H).

The product is stabilised with 2,6-di-tert-butyo-p-cresol and stored cool.

EXAMPLE 9

2,4-Divinyl-6-methylpyridine

The procedure of Example 8 is carried out with 165 g (0.205 mole) of [6-methylpyridine-2,4-diyl-bis(methylene)]bis-triphenylphosphonium dibromide (Example 6). Yield: 25.3 g (85% of theory); b.p. 45°–48° C./9.3 Pa; $n_D^{20}$=1.5682.

¹H-NMR (CDCl₃): δ=2.48 (s; 3H), 5.31 (m, J=1.5 Hz and 10 Hz; 1H), 5.36 (m, J=2 Hz and 10 Hz; 1H), 5.80 (m, J=1.5 Hz and 18 Hz; 1H), 6.12 (m, J=2 Hz and 18 Hz; 1H), 6.51 (m, J=10 Hz and 18 Hz; 1H), 6.75 (m, J=10 Hz and 18 Hz; 1H), 6.88 (s; 1H) and 7.01 ppm (s; 1H).

The product is stabilised with 2,6-di-tert-butyl-p-cresol and stored cool.

EXAMPLE 10

2,4-Divinyl-6-methylpyridine and 2,5-divinyl-6-methylpyridine

Method A

Following the procedure of Example 8, the mixture of isomers of the phosphonium salts obtained in Example 5 are reacted with formaldehyde. From 371 g (0.43 mole) of bisphosphonium salt having a ratio of 57 parts of 2,4,6-substituted pyridine isomer to 43 parts of 2,5,6- substituted pyridine isomer, there are obtained 39.6 g (63.5% of theory) of a mixture of divinyl-6-methylpyridines in which the isomers are approximately in the same ratio. Boiling point: 40°–48° C./20 Pa.

Method B 3.93 g (0.01 mole) of a mixture of isomers of the tetraethyl bisphosphonate obtained in Example 7 are dissolved in 70 ml of dichloroethane. Then 35 ml of 35% aqueous formaldehyde solution, 35 ml of 50% aqueous sodium hydroxide solution of 0.134 g of tetrabutylammonium cyanide are added. In addition, 0.02 g of 2,6-di-tert-butyl-p-cresol and 0.02 g of diisopropylxanthogen disulfide are added as polymerisation inhibitors.

The batch is heated in a steel autoclave for 4 hours to 100° C. The organic phase is then separated and the aqueous phase is washed with dichloroethane. The combined extracts, to which 10 mg of 2,6-di-tert-butyl-p-cresol are added, are concentrated at $1.5 \times 10^3$ Pa. The oily residue is dissolved in semiconcentrated hydrochloric acid and washed with three 100 ml portions of ethyl acetate. A layer of 100 ml of ethyl acetate is added to the aqueous phase, which is then made alkaline with potassium carbonate. The organic phase is separated, dried over sodium sulfate and concentrated at $1.5 \times 10^3$ Pa, affording 2.5 g of an oil which is separated into two fractions by bulb tube distillation. The first fraction (b.p. 70°–120° C./27 Pa) contains 77% (analysis by gas chromatography) of divinyl-6-methylpyridines, and the second fraction (b.p. 230° C./0.13 Pa) contains starting materials and diethyl[monovinyl-6-methylpyridinyl)]-phosphonate.

Method C 2.48 g (13.6 mmoles) of the mixture of isomers consisting of bis(2-hydroxyethyl)-6-methylpyridines obtained in Example 2 are heated slowly to 170° C. at 1.3 Pa over 2.8 g of powdered potassium hydroxide. 1.38 g of distillate are collected during this heating. To this distillate are added 40 ml of diethyl ether and the solution is dried over sodium sulfate and concentrated. The residue is redistilled (bulb tube distillation) over a small amount of powdered potassium hydroxide in the presence of about 10 mg of 2,6-di-tert-butyl-p-cresol at 60°–70° C./27 Pa. Yield: 0.84 g; $n_D^{20} = 1.5721$. A ratio of 5 parts of 2,4,6-substituted pyridine isomer to 1 part of 2,5,6-substituted pyridine isomer is determined by NMR spectroscopy.

Method D

A steel autoclave is charged, under nitrogen, with a mixture of 164 g (4 moles) of acetonitrile, 26 g (0.5 mole) of vinyl acetylene and 1.51 g (0.0065 mole) of cyclopendadienyl-cobalt-cycloocta-(1,5)-diene. The solution is pumped continuously through a tube-shaped pressure reactor with a capacity of about 70 ml. A temperature of 148° C. is kept by thermostatic control of the reactor. The average residence time of the reaction mixture in the reactor is limited to 30 minutes. The pressure in the reactor rises to about $3.5 \times 10^6$ Pa. After the reactor has been substantially discharged, pure acetonitrile is introduced in order to remove the reaction products completely from the reactor. 264 g of a solution are obtained. A main product which is identical to the mixture of isomers prepared by Method A is identified by gas chromatography (OV 101.3%). A yield of 15.6 g (45% of theory) of divinyl-6-methylpyridines is determined by titration with 0.1N perchloric acid in dioxan.

The reaction products are isolated as follows: The bulk of excess acetonitrile is stripped off from the reaction mixture at $1.5 \times 10^3$ Pa and a maximum temperature of 30° C. after addition of about 200 mg of 2,6-di-tert-butyl-p-cresol. The residue is dissolved in dilute hydrochloric acid and washed with two 100 ml portions of ethyl acetate. A layer of about 150 ml of ethyl acetate is added to the aqueous phase, which is then made alkaline by stirring in potassium carbonate. The organic phase is separated and, after addition of about 100 mg of 2,6-di-tert-butyl-p-cresol, dried over sodium sulfate and concentrated at $1.5 \times 10^3$ Pa. The liquid crude product is distilled at about 90° C./27 Pa in a bulb tube. Yield of isolated product: 9.1 g (25% of theory). A ratio of 17 parts of 2,4,6-substituted pyridine isomer to 9 parts of 2,5,6-substituted pyridine isomer is determined by NMR spectroscopy.

EXAMPLE 11

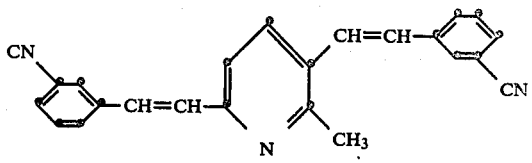

3.64 g (0.02 mole) of 3-bromobenzonitrile are dissolved in 30 ml of N,N-dimethylformamide and 15 ml of triethylamine. To the solution are added 0.09 g (0.4 mmoles) of palladium(II) acetate and 0.25 g (0.8 mmoles) of tri-o-tolylphosphine and the mixture is heated to 100° C. A solution of 1.45 g (0.01 mole) of 2,5-divinyl-6-methylpyridine is added dropwise to the reaction mixture, which is subsequently stirred for 2 hours at 100° C. and then cooled to room temperature. The reaction mixture is filtered and 70 ml of dimethyl ether and 70 ml of $H_2O$ are added to the filtrate. After removal of the water, yellow crystals precipitate from the organic phase. The crystalline solid is washed repeatedly with toluene and ether and then dried, affording 2 g of yellow crystals, corresponding to a yield of 58% of theory.

The compound has the empirical formula $C_{24}H_{17}N_3$. Elemental analysis: calculated: C 82.97% H 4.93% N 12.10%; found: C 83.0% H 5.1% N 11.9%.

The compound has a $\lambda_{max}$ of 362 μm and a $FL_{max}$ of 433 μm.

The spectral data and coloration (degree of whiteness) show that the compound is suitable for use as a fluorescent whitening agent.

What is claimed is:
1. A process for the preparation of a compound of the formula I

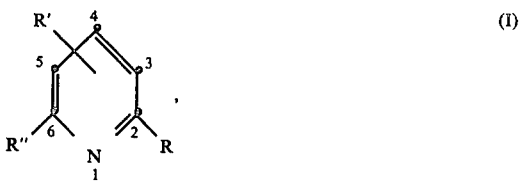

wherein
R' is found in the 4- or 5-position,

R and R' are —CH₂OH, —CH₂CH₂OH, —CH₂C-H₂OCH₂C₆H₅, —CH₂X, —CH₂P⊕(Y)₃X⊖, —CH₂P(O)(C₁₋₃alkoxy)₂ or —CH=CH₂, R" is C₁₋₁₀alkyl, X is a halogen atom, X⊖ is the anion corresponding to X and Y is phenyl which may be substituted by a C₁–C₅alkyl group, which process comprises reacting a compound of the formula II

    (II)

with a compound of the formula III

    (III)

in the temperature range from 40° to 180° C. and in the presence of a cobalt(I) catalyst, to give a compound of the formula IV

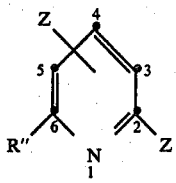    (IV)

wherein R" is as defined for formula I and Z is —CH₂OH, —CH₂CH₂OH or —CH₂CH₂OCH₂C₆H₅, and dehydrating a compound of the formula IV, wherein Z is —CH₂CH₂OH or —CH₂CH₂OCH₂C₆H₅, if desired after previously hydrogenating —CH₂CH₂OCH₂C₆H₅ groups to —CH₂CH₂OH groups, to compounds of the formula I, in which R and R' are —CH=CH₂, and reacting a compound of the formula IV, in which Z is —CH₂OH, by treatment with a halogenating agent, to give a compound of the formula V

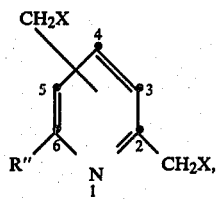    (V)

reacting the compound of the formula V with a compound of the formula VIa and VIb

    (VIa)

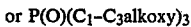    (VIb)

to give a compound of the formula VIIa and VIIb

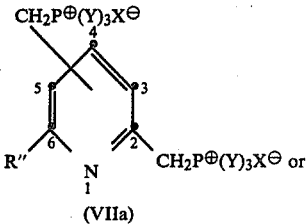

(VIIa)

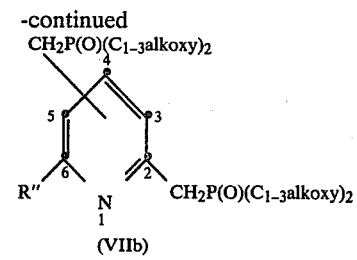

(VIIb)

and reacting the compound of the formula VIIa or VIIb with formaldehyde, in the presence of a base, to give a compound in which R and R' are —CH=CH₂, and R", Y, X and X⊖ are as defined for formula I and the second group Z, —CH₂-halogen, —CH₂P⊕(Y)₃X⊖ or —CH₂-P(O)(C₁–C₃alkoxy)₂ are each linked to the pyridine ring in the 4- or 5-position.

2. A process according to claim 1, which comprises the use of a compound of the formula II, wherein R" is straight chain or branched C₁–C₄alkyl.

3. A process according to claim 1, which comprises the use of a compound of the formula II, wherein R" is methyl.

4. A process according to claim 1, which comprises the use of a compound of the formula III, wherein Z is —CH₂CH₂OH.

5. A process according in claim 1, which comprises the use of a compound of the formula III, wherein Z is —CH₂OH.

6. A process according to claim 1, wherein concentrated aqueous hydrochloric acid is used as halogenating agent.

7. A process according to claim 1, wherein concentrated aqueous hydrobromic acid is used as halogenating agent.

8. A process according to claim 1, wherein the cobalt(I) catalyst is biscyclopentadienylcobalt which may also be substituted at one cyclopentadienyl group, biscyclopentadienyltetraphenylcobalt, cyclopentadienyl-cobalt-cyclooctadiene, η³-cyclooctadienyl-cobalt-cyclooctadiene or methylheptadienyl-cobalt-butadiene.

9. A process according to claim 1, wherein the cobalt(I) catalyst is cyclopentadienyl-cobalt-cyclooctadiene.

10. A process according to claim 1, which comprises the use of a compound of the formula VIa, wherein Y is unsubstituted phenyl.

11. A process according to claim 1, which comprises the use of a compound of the formula VIb, wherein alkoxy is ethoxy or isopropoxy.

12. A process according to claim 1, wherein the cobalt(I) catalyst is used in an amount of 0.1 to 3 mole%, based on the alkylene of the formula III.

13. A process according to claim 1, wherein the cobalt(I) catalyst is used in an amount of 0.1 to 1 mole%, based on the alkyne of the formula III.

14. A process according to claim 1, wherein the co-cyclotrimerisation to give compounds of the formula IV is carried out in the temperature range from 80° to 160° C.

15. A process according to claim 1, wherein an excess of nitrile of the formula II is used.

16. A process for the preparation of a compound of the formula Ia

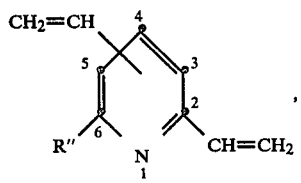

wherein the second vinyl group is bound in the 4- or 5-position and R″ is $C_1$-$C_{10}$alkyl, which process comprises reacting a compound of the formula II $$R''-CN \qquad (II)$$

with vinyl acetylene, in the temperature range from 30° to 170° C. and in the presence of a cobalt(I) catalyst.

17. A compound of the formula I

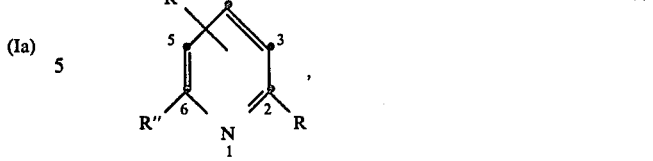

wherein
R′ is bound in the 4- or 5-position,
R and R′ are —$CH_2OH$, —$CH_2CH_2OH$, —$CH_2$-$CH_2OCH_2C_6H_5$, —$CH_2X$, —$CH_2P^{\oplus}(Y)_3X^{\ominus}$, —$CH_2P(O)(C_{1-3}alkoxy)_2$ or —CH=$CH_2$,
R″ is $C_{1-10}$alkyl,
X is a halogen atom,
$X^{\ominus}$ is the anion corresponding to X and
Y is phenyl which may be substituted by a $C_1$-$C_5$alkyl group,
with the exception of 2,4-bis(β-hydroxymethyl)-6-methylpyridine and 2,4-divinyl-6-methylpyridine.

18. 2,5-Divinyl-6-methylpyridine according to claim 17.

19. 2,5-Bis(hydroxymethyl)-6-methylpyridine according to claim 17.

20. 2,4-Bis(hydroxymethyl)-6-methylpyridine according to claim 17.

* * * * *